(12) United States Patent
Moreno-Barragan

(10) Patent No.: US 6,574,613 B1
(45) Date of Patent: Jun. 3, 2003

(54) SYSTEM AND METHOD FOR DIAGNOSING JET ENGINE CONDITIONS

(76) Inventor: Jorge Moreno-Barragan, Bauschinger Str. 17, D-80997 München (DE)

( * ) Notice: Subject to any disclaimer, the term of this patent is extended or adjusted under 35 U.S.C. 154(b) by 0 days.

(21) Appl. No.: 09/403,878

(22) PCT Filed: Feb. 24, 1999

(86) PCT No.: PCT/DE99/00491
§ 371 (c)(1),
(2), (4) Date: Mar. 2, 2000

(87) PCT Pub. No.: WO99/44106
PCT Pub. Date: Sep. 2, 1999

(30) Foreign Application Priority Data

Feb. 27, 1998 (DE) .......................... 198 08 197

(51) Int. Cl.[7] .............................................. G06F 15/18
(52) U.S. Cl. ................... 706/16; 706/2; 706/20; 706/905; 706/913
(58) Field of Search .............................. 706/16, 20, 15, 706/905, 913, 911, 2; 73/117, 3, 116; 700/48, 47, 49, 291; 701/27, 29, 106; 244/62

(56) References Cited

U.S. PATENT DOCUMENTS

| | | | | |
|---|---|---|---|---|
| 4,215,404 A | * | 7/1980 | Bukhtiyarov et al. ........ | 701/102 |
| 5,041,976 A | * | 8/1991 | Marko et al. ................. | 701/29 |
| H1006 H | * | 12/1991 | Zwicke ........................ | 700/298 |
| 5,093,792 A | * | 3/1992 | Taki et al. .................... | 706/20 |
| 5,247,445 A | * | 9/1993 | Miyano et al. ............... | 701/115 |
| 5,313,407 A | * | 5/1994 | Tiernan et al. ............... | 700/280 |
| 5,361,628 A | * | 11/1994 | Marko et al. ................. | 73/116 |
| 5,566,092 A | * | 10/1996 | Wang et al. .................. | 702/185 |
| 5,732,382 A | * | 3/1998 | Puskorius et al. ........... | 701/110 |
| 5,821,412 A | * | 10/1998 | Bryant et al. ................ | 73/117.3 |
| 5,869,752 A | * | 2/1999 | Klauber et al. .............. | 73/116 |
| 6,175,787 B1 | * | 1/2001 | Breed .......................... | 701/29 |

FOREIGN PATENT DOCUMENTS

| | | | | |
|---|---|---|---|---|
| DE | 297 00 028 | | 4/1997 | ......... G05B/19/406 |
| EP | 0 805 382 | | 11/1997 | ......... G05B/19/406 |

OTHER PUBLICATIONS

Dietz et al., Pattern–Based Fault Diagnosis Using Neural Networks, Proceedings of the 1st International Conference on Industrial and Engineering Application of Aritifical Intelligence and Expert Systems–vol. 1, 1988, pp. 13–23.*

Long et al., A Neural Network Based Receding Horizon Optimal (RHO) Controller, Proceedings of the American Control Conference, vol. 3, Jun. 1997, pp. 1994–1995.*

Troudet et al., A Real Time Neural Net Estimator of Fatigue Life, 1990 IJCNN International Conference on Neural Networks, vol. 2, Jun. 1990, pp.59–64.*

(List continued on next page.)

Primary Examiner—John A. Follansbee
Assistant Examiner—Kelvin Booker

(57) ABSTRACT

A system and a method for diagnosis of engine conditions are proposed. In particular, the system and the method are directed to an extraction of features from different information sources and to their processing. These features, together with a series connection of two neural networks, form the crux of the system and method, so that a dependable diagnosis of engine conditions, particularly an error recognition is possible. As a result thereof, maintenance corresponding to the current engine condition is enabled.

17 Claims, 2 Drawing Sheets

OTHER PUBLICATIONS

Gupta et al., Hierarchical Representation and Machine Learning From Faulty Jet Engine Behavioral Examples To Detect Real Time Abnormal Conditions, ACM 1988, pp. 710–720.*

Nairac et al., Choosing An Apporpriate Model for Novelty Detection, 5th International Conference on Artificial Neural Networks, Jul. 1997, pp. 117–122.*

Tarassenko et al., Novelty Detection in Jet Engines, IEE Colloquium on Condition Monitoring: Machinery, External Structures and Health, Apr. 1999, pp. 4/1–4/5.*

Cuomo et al., Neural System for Tracking and Classification of Primary Radar Echo Signals, Proceedings of the 1995 URSI International Symposium on Signals, Systems, and Electronics, Oct. 1995, pp. 509–512.*

Peck et al., SSME Parameter Model Input Selection Using Genetic Algorithms, IEEE Transactions on Aerospace and Electroni Systems, vol. 32, No. 1, Jan.1996, pp. 199–212.*

Dietz et al., Space Shuttle main Engine Component Assembly, Assignment and Scheduling Expert System, Proceedings of the 2nd Intl Conf on Industrial and Engineering Applications of AI and Expert Systems–vol. 1, 1989, pp. 356–363.*

Gupta et al.; "LEADER– An Integrated Engine Behavior and Design Analysis Based Real–Time Fault Diagnostic Expert System for Space Shuttle Main Engine". $2^{nd}$ International Conference on Industrial and Engineering Applications of AI, May 1989, p. 135–145.*

Ulug, M.E..; "A Hybrid Expert System Combining Ai Techniques with a Neural–Net". Proceedings of the 2nd International Conference on Industrial and Engineering Applications of AI, May 1989, p. 305–309.*

Marko et al.; "Neural Network Application to Comprehensive Engine Diagnostics", IEEE Conference on Systems, Man and Cybernetics, Oct. 1992, vol. 2, p. 1016–1022.*

* cited by examiner

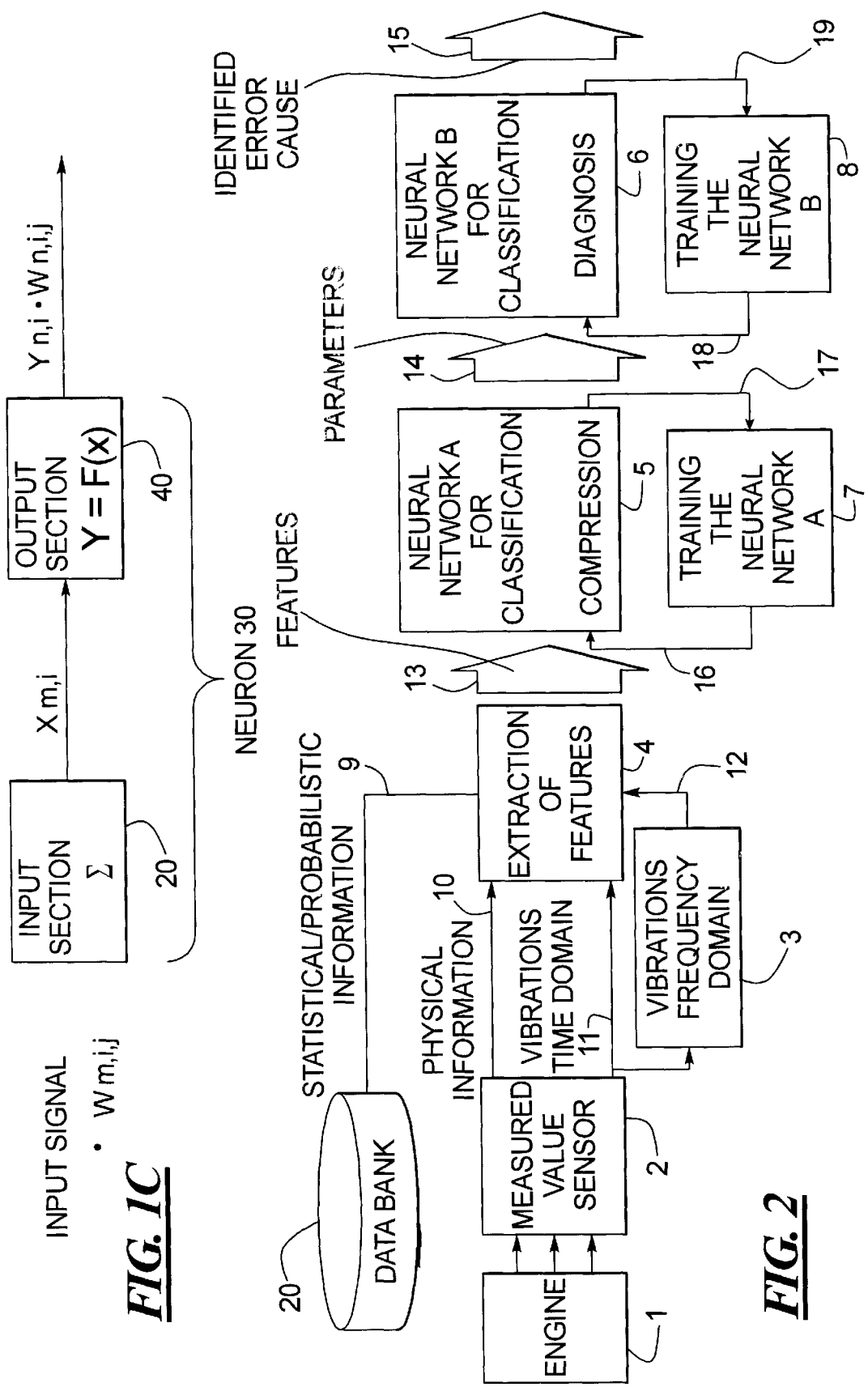

SYSTEM AND METHOD FOR DIAGNOSING JET ENGINE CONDITIONS

FIELD OF THE INVENTION

The invention is directed to a system and a method for diagnosis of engine conditions.

BACKGROUND OF THE INVENTION

Traditionally, the diagnosis of engine conditions utilizes vibration signals on the basis of amplitude limits. The vibration amplitude limits have been derived from general experience and/or on the basis of features from vibration signatures, from the experience deriving from events during the development phase or, respectively, the experience from the certification or testing process.

Costly and time-consuming modifications in mass production of engines usually ensue.

The vibration diagnosis has been implemented by variously qualified specialist teams without a targeted exchange of experience between operators and manufacturers of engines and without systematic acquisition and interpretation of errors, side-effects or, respectively, symptoms and their causes.

In the previously standard vibration diagnosis of engine conditions, there is thus, among other things, the problem that few measuring positions are contrasted to only a limited amount of information for interpretation. There are in fact error catalogs from the development phase; these, however, are usually full of gaps. The influence of a great number of parameters such as, for example, construction standards, tolerances, size and position of unbalanced masses, temperature effects, performance and flight parameters, etc., as well as non-linearities and measuring imprecisions, remain largely unconsidered.

Given this type of vibration diagnosis, dangerous vibration conditions can continue to exist unrecognized during operation. More serious secondary damage due to late recognition can occur and the outlay for maintenance increases since it is usually necessary to dismantle an engine.

SUMMARY OF THE INVENTION

The present invention pertains to systems and a methods for diagnosis of engine conditions. The systems and methods are directed to extraction of features or parameters from different information sources and to processing of the features. These features, together with a series connection of two neural networks, provide a dependable diagnosis of engine conditions, particularly error recognition.

In an embodiment of the present invention, a system for diagnosis of engine conditions has:

a means for supplying statistical/probabilistic information about the error quota of individual engine components resulting from an evaluation of a corresponding data bank and/or a plurality of measurement sensors for acquiring physical information such as, for example, pressures and temperatures in various engine levels and, moreover, parameters from a particle analysis in used oil and in engine exhaust gases as well as parameters from an analysis of the gas path;

a plurality of measurement sensors for acquiring vibration information in the time domain from an engine;

a vibration analysis means for generating vibration information in the frequency domain from the vibration information in the time domain;

a module for feature extraction for processing the physical information and/or the statistical/probabilistic information and the vibration information in the time and frequency domain and for the extraction of a number of features that comprehensively describe the engine condition;

a first neural network to which the features are applied for classification of the features, for identification of relationships and dependencies between features and for corresponding implementation of an information compression and for output of parameters, whereby the first neural network comprises an input layer, one or more intermediate, layers and an output layer of neurons, whereby the input layer comprises more neurons than the intermediate layer(s) and this in turn comprises more neurons than the output layer, and the neurons of a layer are connected via a plurality of connecting elements having variable weighting coefficients;

a first training means for supplying training input signals to the first neural network and for comparison of the output signal output by the first neural network in response thereto to a training input signal and for the modification of variable weighting coefficients of the first neural network by means of application of a predetermined training algorithm corresponding to the differences between the training input signal and the output signal or for realizing a non-monitored training of the first neural network with the assistance of the training input signals by themselves;

a second neural network to which the parameters output by the first neural network are applied for classification of the parameters, for recognition of relationships between the parameters and specific error constellations, for corresponding implementation of an information linkage and for output of a diagnosis signal, whereby the second neural network comprises an input layer, one or more intermediate layers and an output layer of neurons, whereby the input and the output layer comprise fewer neurons than the intermediate layer(s), and the neurons of a layer are connected to the neurons of the layer following thereupon via a plurality of connecting elements having variable weighting coefficients; and a second training means for supplying training input signals to the second neural network and for comparing the output signal obtained from the second neural network in response thereto to a training input signal and for modifying variable weighting coefficients of the second neural network by means of applying a predetermined training algorithm corresponding to the differences between the training input signal and the output signal.

In an embodiment of the present invention, the module for feature extraction employs physical parameters such as oil consumption given specific engine runs, power reference numbers such as pressure and temperature in specific engine levels, parameters from a particle analysis in used oil and in engine exhaust gases as well as parameters from an analysis of the gas path.

In an embodiment of the present invention, the module for feature extraction employs methods that are standard for speech recognition, and extracts effective values, properties of the envelopes, modulations, absolute values, performance analyses, statistical parameters, distribution functions, wavelet analysis, etc., of the vibration information in the time domain as features.

In an embodiment of the present invention, the vibration analysis means handles the vibration signals in the time domain and determines corresponding vibration information in the frequency domain therefrom.

In an embodiment of the present invention, the module for feature extraction employs an information presentation in the form of what is referred to as a waterfall diagram, handles this information presentation with image processing methods and determines corresponding features therefrom from the vibration information in the frequency domain.

In an embodiment of the present invention, the module for feature extraction also implements geometrical considerations of the overall image or specific image regions; and/or the module for feature extraction also considers what are referred to as "skylines" of the waterfall diagram from the perspective of the frequency or, respectively, of the time/speed access.

In an embodiment of the present invention, the module for feature extraction also numerically acquires the vibration information of the waterfall diagrams; and utilizes methods from matrix and vector calculation or methods for system identification in the frequency domain for acquiring features from the vibration information in the frequency domain and/or utilizes transfer functions as well as a distribution analysis of the numerical data.

In an embodiment of the present invention, the neural networks in combination with fuzzy logic or pure fuzzy logic circuits are provided instead of the first and second neural networks.

In an embodiment of the present invention, a method for diagnosis of engine conditions has the steps:

supplying statistical/probabilistic information about the error quota of individual engine components resulting from an evaluation of a corresponding data bank, and/or acquiring physical information such as, for example, pressures and temperatures in various engine levels with a plurality of measurement sensors, as well as parameters from a particle analysis in used oil and in engine exhaust gases as well as parameters from an analysis of the gas path, and/or acquiring vibration information in the time domain from an engine with a plurality of measurement sensors;

generating vibration information in the frequency domain from the vibration information in the time domain with a vibration analysis means;

processing the physical information and/or the statistical/probabilistic information and/or the vibration information in the time and frequency domain and extracting a number of features that comprehensively describe the engine condition with a module for feature extraction;

classification of the features, identification of relationships and dependencies between features and corresponding implementation of an information compression and output of parameters by a first neural network to which the features are applied, whereby the first neural network comprises an input layer, one or more intermediate layers and an output layer, whereby the input layer comprises more neurons than the intermediate layer(s) and this in turn comprises more neurons than the output layer, and the neurons of a layer are connected via a plurality of connecting elements having variable weighting coefficients;

supplying training input signals to the first neural network and comparing the output signal output in response thereto by the first neural network to a training input signal and modifying variable weighting coefficients of the first neural network by means of application of a predetermined training algorithm corresponding to the differences between the training input signal and the output signal or for realizing a non-monitored training of the first neural network with the assistance of a training input signals by themselves with a first training means;

classification of the parameters, recognition of relationships between the parameters and specific error constellations, corresponding implementation of an information linkage and output of a diagnosis signal by means of a second neural network to which the parameters output by the first neural network are applied, whereby the second neural network comprises an input layer, one or more intermediate layers and an output layer of neurons, whereby the input and the output layer comprise fewer neurons than the intermediate layer(s), and the neurons of a layer are connected to the neurons of the layer following thereupon via a plurality of connecting elements having variable weighting coefficients; and supplying training input signals to the second neural network and comparing the output signal obtained in response thereto from the second neural network to a training input signal, and modifying; variable weighting coefficients of the second neural network by means of application of a predetermined training algorithm corresponding to the differences between the training input signal and the output signal with a second training means.

In an embodiment of the present invention, the acquired, physical parameters are an all consumption at specific engine runs, power reference numbers such as pressure and temperature in specific engine levels, parameters from a particle analysis in used oil and in engine exhaust gases as well as parameters from an analysis of the gas path.

In an embodiment of the present invention, specific engine components or parts are, for example, classified as especially susceptible in the feature extraction on the basis of the statistical/probabilistic information and these information are output in the form of features.

In an embodiment of the present invention, methods as standard for speech recognition are employed in the processing of the information and extraction of features, and effective values, properties of the envelopes, modulations, absolute values, power analyses, statistical parameters, distribution functions, wavelet analysis, etc., of the vibration information in the time domain are extracted as features.

In an embodiment of the present invention, the vibration information in the time domain is processed with a vibration analysis means and corresponding vibration information in the frequency domain are determined therefrom.

In an embodiment of the present invention, an information presentation in the form of what is referred to as a waterfall diagram is employed when processing vibration information in the frequency domain, this information presentation being handled with image processing methods and corresponding features from the vibration information in the frequency domain being determined therefrom.

In an embodiment of the present invention, geometrical considerations of the overall image or of specific image regions are implemented as well when processing vibration information in the frequency domain, and/or what are referred to as "skylines" of the waterfall diagram are also extracted when processing the vibration information in the frequency domain viewed from the perspective of the frequency or, respectively, of the time/speed access and corresponding features are extracted therefrom.

In an embodiment of the present invention, the information of the waterfall diagrams are also numerically acquired when processing vibration information in the frequency domain, and methods from matrix and vector calculation or methods for system identification in the frequency domain are utilized for acquiring vibration information in the frequency domain and/or transfer functions as well as a distribution analysis of the numerical data are utilized.

In an embodiment of the present invention, the classification, identification, information compression and output of parameters and the classification, recognition of relationships, information linkage and output of a diagnosis signal is implemented by neural networks in combination with fuzzy logic or by pure fuzzy logic circuits instead of by the first and second neural networks.

An object of the present invention is therefore to create a system and a method for diagnosis of engine conditions, whereby the dependability is enhanced on the basis of a recognition of dangerous vibration conditions, more serious secondary damage is avoided due to an early error recognition, the outlay for maintenance is reduced by targeted elimination of the causes of vibration and maintenance ensues according to the current condition of the engine (i. e., "on-condition").

Objects and advantages of the present invention will become apparent upon reading this disclosure including the appended claims and with reference to the accompanying drawings. The objects and advantages may be desired, but may not necessarily be required to practice the present invention.

FIG. 1C is a schematic illustration of a structure of a neuron unit that is employed in the networks according to FIG. 1A and FIG. 1B; and FIG. 2 is a block circuit diagram for illustrating a structure of the inventive system for diagnosing engine conditions.

DETAILED DESCRIPTION OF PRESENTLY PREFERRED EMBODIMENTS

Figure 1A:
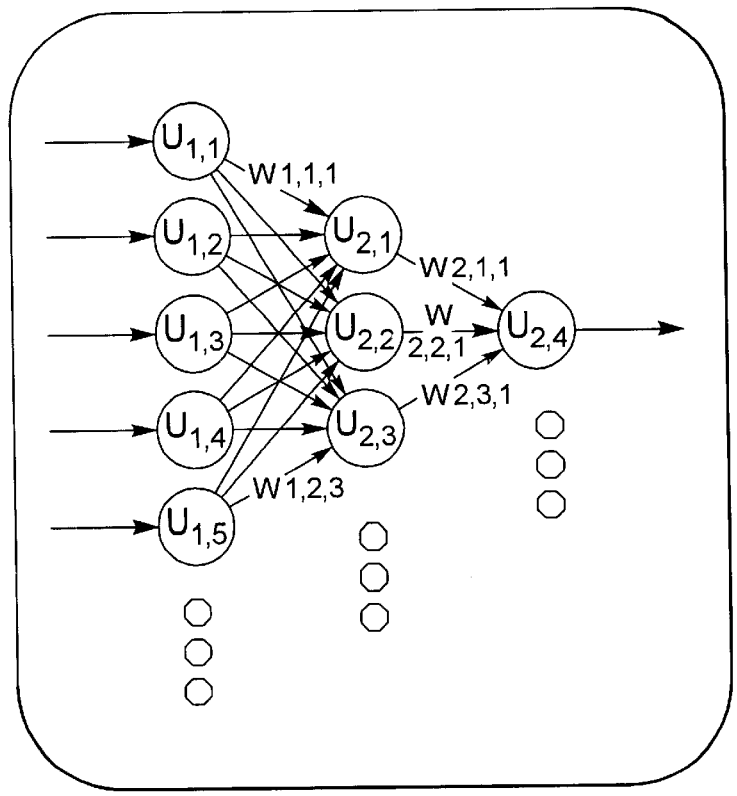
FIG. 1A is a schematic illustration of a structure of a neural multi-layer network for information compression.

Although the present invention can be made in many different forms, the presently preferred embodiments are described in this disclosure and shown in the attached drawings. This disclosure exemplifies the principles of the present invention and does not limit the broad aspects of the invention only to the illustrated embodiments.

The focus of the invention lies in a method and an apparatus for the extraction of features from different information sources and their processing. These features, that characterize the engine condition in comprehensive fashion, form the crux of the system together with a series connection of two neural networks.

Both a simulation as well as a measurement can be employed for generating vibration patterns (training data) for the diagnosis of engine conditions. Both methods have their advantages and disadvantages, these being explained below.

In a simulation, it is advantageous that an analysis of various predefined error cases and, moreover, a combination of errors are utilized. The evaluation can thereby ensue at arbitrary positions the number of which is only limited by the plurality of degrees of freedom of the simulation model. Extreme, destructive cases can be analyzed. Among other things, it is advantageous to use pure signals without noise. Simulations of engine runs are comparatively cost-beneficial.

What is disadvantageous in the simulation, however, is that it is subject to certain assumptions, for example in the modeling of connections and damping properties, etc. Included among the other disadvantages of simulation are the limited validity thereof, for example only for a specific frequency band (normally the lower frequency range) and that some effects can only be taken into consideration with extremely great effort. Also, the simulation models only describe certain properties of the structure with a high precision. Other properties such as, for example, thermal influences, etc., are only globally taken into consideration by contrast.

Compared to simulation, measurement has the following advantages. The actual, current structure is employed, and no physical idealization thereof. Particularly in the development and certification processes, certain load cases are analyzed that correspond to specific errors, for example blade loss at various stages of the individual components of the engine. Moreover, additional operating parameters can be taken into consideration in measurements. A number of additional parameters can be registered, particularly given investigations during operation.

However, problems also derive ir measurement. The imprecision or, respectively, scatter of the measurement has a disadvantageous effect, as does measuring errors or noise effects. Additionally, the individuality of the engines and the variable reference conditions are problematical. Observation can only be implemented at a few fixed positions.

The following considerations thus derive for overcoming these disadvantages and problems.

An extensive, numerical generation of vibration identification signals should ensue, which should be accompanied by a generation of experimental signatures. A definition of parameters that are to be observed and employed for diagnosis as well as a creation of an error catalog are required for this purpose. The errors to be identified should be defined and an analysis of connections or, respectively, a relationship between errors should occur.

An extraction of features and an analysis of connections or, respectively, relationships between symptoms, side effects or, respectively, indications is also desired. Parameters should be identified and engine models developed, and connections or, respectively, relationships between errors and side effects or, respectively, indications should be produced.

Further, a development of comprehensive diagnosis systems on the basis of neural networks taking various physical information (vibrations, performance features, temperature, etc.) and statistical or, respectively, probabilistic information sources into consideration is desired.

The properties of the neural networks such as, for example, the type or, respectively, the nature, the architecture, the training method, etc., should be defined. Over and above this, investigations about a possible application of neural networks in combination with fuzzy logic should ensue. Finally, the simulation models or, respectively, methods and the mensurational techniques are optimized via sensitivity and correlation analysis.

The main problems that occur given mensurational observations are the data scatter, the identification of noise data, the limited data sets for a complete analysis and the varying reference condition for each engine. Possible solutions of the problems are a model allocation, a classification and an identification of information with neural or, respectively, neuro-fuzzy methods.

Inventively, it is not, as traditionally, only the acquired vibration signals of the engine that are inventively employed for diagnosis in the diagnosis of engine conditions. Rather, other operating parameters such as, for example, altitude, temperature, etc. that likewise co-influence the condition of the engine are employed. Further, statistical and probabilistic observations should be additionally taken into consideration.

The diagnosis of the engine condition thereby ensues upon employment of a learning, intelligent system. This system is utilized from the development phase up to mass production. Additional physical information such as operating parameters, temperatures, performance parameters, etc., are employed for the diagnosis. The current structural standard and the prior history of the engine as well as the symptoms and their verified error causes are systematically registered and interpreted in the inventive system and method.

In particular, the intelligent system is trained upon employment of physical simulation models, whereby the physical models are improved iteratively or, respectively, step-by-step upon employment of a correlation with the measurements. In addition, the intelligent system is trained with the assistance of actual or, respectively, real events and occurrences.

Moreover, the error instances of using customers or users are collected and interpreted by the producers upon employment of a common data base or, respectively, data bank.

Neural networks are employed in such an intelligent system. A neural network is composed of a plurality of neurons, each neuron having a non-linear input/output characteristic and being connected to one another by connecting elements having respectively mutually independent weighting coefficients. The weighting coefficients can be modified with a learning procedure. The output signal of the neural network is compared to a known value (training value) on the basis of a particular combination of input values, the known value corresponding to these input values. A modification of the weighting coefficients is derived from this comparison such as, for example, in order to bring the output value of the neural network closer to the training value. A learning algorithm or, respectively, calculating method is employed for this purpose. The learning process is successively repeated for a plurality of different training values and corresponding input value combinations. This is particularly true of the neural network according to FIG. 1B in which training, for example, the method of monitored "back propagation" can be employed. Further, there is also the possibility of utilizing some other method for training the neural networks. What is involved, for example, are non-monitored methods (for example, methods of self-organizing cards of Koherson that, in particular, are employed for classification jobs as in the neural network of FIG. 1A.

Figure 1B:
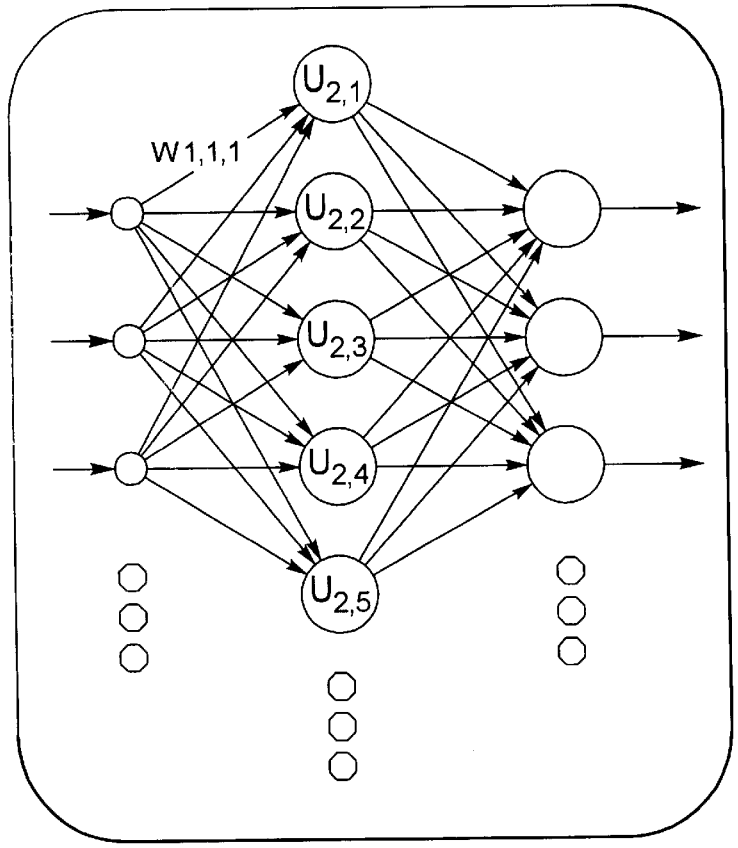
FIG. 1B is a schematic illustration of a structure of a neural multi-layer network for information linkage.

A neural multi-layer network according to FIG. 1A and FIG. 1B is formed of successive layers of neurons with intermediate connections on the basis of connecting elements that are connected between the neurons of one layer and neurons of preceding and following layers. The connecting elements multiply the output signals with weighting coefficients $W_{n,i,j}$ or, respectively, $W_{n,j,k}$. During the training procedure of a neural network, these weighting coefficients $W_{n,i,j}$ or, respectively, $W_{n,j,k}$ are capable of being modified and are determined mutually independently. The values of the weighting coefficients $W_{n,i,j}$ that connect the input layer to the intermediate layer can be considered to be the respective coupling intensities between neurons of the intermediate layer $U_{2,j}$ and the neurons of the input layer $U_{1,i}$. When the output layer $U_{3,k}$ of the neural network is composed of only a single neuron $U_{3,l}$, an individual output value from the last neuron of the neural network responding to a specific combination of input signal values supplied to the input layer of the neural network is generated.

FIG. 1C shows a neuron 30 that can be considered as being composed of an input section 20 and an output section 40. The input section 20 sums up the weighted input signal values supplied to it, whereby each of these input signal values is multiplied by a corresponding weighting coefficient $W_{m,i,j}$. The summed-up output signal that derives and that is generated by the input section 20 of the neuron 30 is referenced $X_{m,i}$ and supplied to the output section 40 of the neuron. The output section 40 carries out a processing corresponding to a non-linear function $Y=F(x)$ in order to obtain the output signal $Y_{n,i}$ that is supplied to one or more neurons of the following layer after it was multiplied by respective weighting coefficients.

The inventive system and method for diagnosis of engine conditions shall now be described below with reference to FIG. 2.

Via measurement sensors 2, the inventive system and method receives physical information 10 such as, for example, pressure and temperature in various levels of an engine 1 as well as parameters from the gas tracking within the engine 1 and from the particle analysis in the used oil. Further, the system receives vibration information in the time domain 11 and, after processing thereof with a vibration analysis means 3, receives information in the frequency domain 12. Additionally, information is transmitted to the system that results from statistical and probabilistic observations 9 from data of a corresponding data bank 20. Upon application of specific algorithms features 13 that comprehensively characterize the engine are extracted from this plethora of information by a module for feature extraction 4.

The inventive system or, respectively, method employs a first neural network 5 that comprises more neurons in the input layer than in the output layer. The job of this network is to classify the supplied features 13 and, to identify relationships and dependencies between the features. Groups of features are formed that are taken into consideration in the course of the further process on the basis of selected "representatives", that is the parameters 14. A data compression is thus achieved by elimination of redundant information.

The first neural network 5 is trained by a first training means 7 upon application of various methods. Among others, the method of "back propagation" with the data sets 16 and 17 is employed; however, the method of "self-organizing cards" is also utilized.

A second neural network 6 is also provided in the inventive system and method. Input signals of the second, following neural network 6 are the identifying parameters 14. The job of this second neural network is the classification and recognition of relationships between the parameters 14 and specific error constellations 15. This procedure is called diagnosis within the scope of the inventive system, since the errors 15 are causally associated via the parameters 14 and these are in turn causally associated via the features 13 with physically interpretable properties of the engine 1.

The various layers of the second neural network 6 are respectively composed of a number of neurons. As usual in classification processes, the plurality of covered layers will be relatively low (one or two layers). The plurality of neurons, however, will usually be greater than those of the outer layers. The output signal of the second neural network is a diagnosis signal which indicates a specific error constellation 15.

The training of the second neural network by a second training means 8 is implemented with the assistance of the monitored "back propagation" method. Known errors 19 and their symptoms are thereby utilized in the form of parameters 18.

Which input signals are supplied to the module for feature extraction 4 shall now be discussed in greater detail. As already mentioned above, these input data are vibration signals in the time and frequency domain 11 or, respectively, 12 and, additionally, physical 10 as well as statistical/probabilistic 9 observation parameters. These information components are separately processed in the module for feature extraction; however, common identifiers for further processing are provided.

Regarding, the vibration signals in the time domain 11, methods and techniques are employed which are standard for speech recognition. Moreover, the effective value "RMS=root mean square), envelopes, modulations, absolute values, performance analysis, statistical parameters (standard deviations, etc.), distribution functions, wavelet analysis, etc. of the vibration signals in the time domain are employed as indicators.

By contrast, a presentation in the form of what is referred to as a waterfall diagram is selected for the vibration signals in the frequency domain 12. This graphic information presentation is then handled with image processing methods and corresponding features are sorted out therefrom. A global observation is thus realized since the same weighting is used for the processing of all regions of the image (waterfall diagram). Further, geometrical observations are implemented in order to generate indicators such as, for example, the center of gravity of the overall image or center of gravities of specific image regions that are defined according to specific physical considerations (for example, sub-harmonic or super-harmonic range). What are referred to as the "skylines" of the waterfall diagram supply additional image features viewed from the perspective of the frequency or, respectively, of the time/speed axis.

The information of the waterfall diagrams is also numerically acquired. The additional possibility thus derives of utilizing methods from matrix or vector calculation (various norms, lengths, etc.) such as, for example, determination of maximum values, average values, aggregate norms, Euclidian norms, correlation coefficients, regression coefficients, standard deviations, etc., for acquiring indicators. Further, information which allow the generation of additional features are extracted from the development of the amplitudes of the vibrations allocated to the operating speed of the respective rotor, the multiples thereof and combinations thereof. Another alternative of processing the numerical information is the application of methods for system identification (direct estimation method, etc.) in the frequency domain related to individual spectra (i.e., quasi-constant speed) and/or to the curves of the speed harmonics. Taking transfer functions as well as a distribution analysis of the numerical data into consideration supplies additional indicators from the vibration signals in the frequency domain.

Observations of additional physical parameters 10 are a completely different source of features. This group of parameters includes the oil consumption given specific engine runs, power reference numbers such as pressure and temperature in specific engine levels, particle analysis in the used oil and in the engine exhaust gases as well as analysis of the gas path. Another alternative derives from the statistical or, respectively, probabilistic consideration of the errors 9. Specific engine components or parts can be classified as especially susceptible with the assistance of this analysis. This information is employed in the form of features.

The features 13 resulting from the corresponding module for feature extraction 4 are then the input data of the input layer of the first neural network 5. The job of this network is the compression of the definitely extensive input information and the generation of largely independent parameters 14.

The parameters 14 output by the first neural network 5 are supplied to the second neural network 6 and this subsequently outputs a corresponding diagnosis signal (error signal) 15.

By employing the two neural networks with the inventive system or, respectively, method, a dependable diagnosis of the engine condition can thus be achieved.

Instead of the two neural networks, neural networks can also be employed in combination with fuzzy logic or pure fuzzy logic circuits can be employed.

While the presently preferred embodiments have been illustrated and described, numerous changes, in modifications can be made without significantly departing from the spirit and scope of this invention. Therefore, the inventor intends that such changes and modifications are covered by the appended claims.

What is claimed is:

1. A system for diagnosis of jet engine conditions, comprising:

means for supplying statistical information about an error quota of individual jet engine components from a data bank;

a plurality of measurement sensors for acquiring physical information about the jet engine selected from pressures and temperatures in various engine levels and parameters from a particle analysis in used oil and in engine exhaust gases as well as parameters from an analysis of the gas path;

a plurality of measurement sensors for acquiring vibration information in the time domain from the jet engine;

vibration analysis means for generating vibration information in the frequency domain from the vibration information in the time domain;

a module for feature extraction for processing the physical information and/or the statistical information and the vibration information in the time and frequency domain and for the extraction of a number of features that describe the jet engine condition;

a first neural network to which the features are applied for classification of the features, for identification of relationships and dependencies between features and for corresponding implementation of an information compression and for output of parameters, whereby the first neural network comprises an input layer, an intermediate layer and an output layer of neurons, the input layer comprises more neurons than the intermediate layer and the intermediate layer comprises more neurons than the output layer, and the neurons of the input layer are connected to the neurons of the intermediate layer, which are connected to the neurons of the output layer via a plurality of connecting elements having variable weighting coefficients;

first training means for supplying training input signals to the first neural network and for comparison of an output signal being outputted by the first neural network in response thereto to a training input signal and for the modification of variable weighting coefficients of the first neural network;

a second neural network to which the parameters output by the first neural network are applied for classification of the parameters, for recognition of relationships between the parameters and specific error constellations, for corresponding implementation of an information linkage and for output of a diagnosis signal, the second neural network comprises an input layer, an intermediate layer and an output layer of neurons, the input layer and the output layer comprise fewer neurons than the intermediate layer, and the neurons of the input layer are connected to the neurons of the intermediate layer, which are connected to the neurons of the output layer via a plurality of connecting elements having variable weighting coefficients; and a second training means for supplying training input signals to the second neural network and for comparing the output signal obtained from the second neural network in response thereto to a training input signal and for modifying variable weighting coefficients of the second neural network.

2. A system according to claim 1, wherein the module for feature extraction employs physical parameters selected from a group consisting of oil consumption for specific engine runs, power reference numbers including pressure and temperature in specific engine levels, parameters from a particle analysis in used oil and in engine exhaust gases as well as parameters from an analysis of the gas path.

3. A system according to claim 1, wherein the module for feature extraction extracts features selected from a group consisting of effective values, properties of envelopes, modulations, absolute values, performance analyses, statistical parameters, distribution functions and wavelet analysis of the vibration information in the time domain.

4. A system according to claim 1, wherein the vibration analysis means handles the vibration signals in the time domain and determines corresponding vibration information in the frequency domain therefrom.

5. A system according to claim 1, wherein the module for feature extraction employs an information presentation in the form of a waterfall diagram, handles this information presentation with image processing methods and determines corresponding features therefrom from the vibration information in the frequency domain.

6. A system according to claim 1, wherein the module for feature extraction also implements geometrical considerations of overall image or specific image regions.

7. A system according to claim 1, wherein the module for feature extraction also numerically acquires the vibration information of waterfall diagrams; and utilizes methods selected from methods from matrix and vector calculation and methods for system identification in the frequency domain for acquiring features from the vibration information in the frequency domain.

8. A system according to claim 1, wherein neural networks in combination with fuzzy logic or pure fuzzy logic circuits are provided instead of the first and second neural networks.

9. A method for diagnosis of jet engine conditions, comprising the steps of:

supplying statistical information about an error quota of individual jet engine components resulting from an evaluation of a data band;

acquiring physical information about the jet engine selected from pressures and temperatures in various engine levels with a plurality of measurement sensors, parameters from a particle analysis in used oil and in jet engine exhaust gases as well as parameters from an analysis of the gas path;

acquiring vibration information in the time domain from the jet engine with a plurality of measurement sensors;

generating vibration information in the frequency domain from the vibration information in the time domain with vibration analysis means;

processing the physical information and/or the statistical information and the vibration information in the time and frequency domain and extracting a number of features that describe the jet engine condition with a module for feature extraction;

classifying the features and identifying relationships and dependencies between features and corresponding implementation of an information compression and output of parameters by a first neural network to which the features are applied, wherein the first neural network comprises an input layer, an intermediate layer and an output layer, the input layer comprises more neurons than the intermediate layer and the intermediate layer comprises more neurons than the output layer and the neurons of each layer are connected to the neurons of adjacent layers via a plurality of connecting elements having variable weighting coefficients;

supplying training input signals to the first neural network and comparing an output signal being outputted in response thereto by the first neural network to a training input signal and modifying the variable weighting coefficients of the first neural network;

classifying the parameters, recognition of relationships between the parameters and specific error constellations, corresponding implementation of an information linkage and output of a diagnosis signal by means of a second neural network to which the parameters being outputted by the first neural network are applied, wherein the second neural network comprises an input layer, an intermediate layer and an output layer of neurons, wherein the input layer and the output layer have fewer neurons than the intermediate layer, and the neurons of each layer are connected to the neurons of adjacent layers via a plurality of connecting elements having variable weighting coefficients;

supplying training input signals to the second neural network and comparing an output signal obtained in response thereto from the second neural network to a training input signal, and modifying the variable weighting coefficients of the second neural network.

10. A method according to claim 9, wherein the acquired, physical parameters are selected from all consumption at specific engine runs, power reference numbers including pressure and temperature in specific engine levels, parameters from a particle analysis in used oil and in jet engine exhaust gases as well as parameters from an analysis of the gas path.

11. A method according to claim 9, wherein specific engine components are classified as susceptible in the feature extraction on the basis of the statistical information and are output in the form of features.

12. A method according to claim 9, wherein the extracted features are selected from a group consisting of effective values, properties of envelopes, modulations, absolute values, power analyses, statistical parameters, distribution functions and wavelet analysis of the vibration information in the time domain.

13. A method according to claim 9, wherein the vibration information in the time domain is processed with vibration analysis means and corresponding vibration information in the frequency domain are determined therefrom.

14. A method according to claim 9, wherein an information presentation in the form of a waterfall diagram is employed when processing vibration information in the frequency domain, this information presentation being handled with image processing methods and corresponding features from the vibration information in the frequency domain being determined therefrom.

15. A method according to claim 9, wherein geometrical considerations of overall image or of specific image regions are implemented as well when processing vibration information in the frequency domain.

16. A method according to claim 9, wherein information of waterfall diagrams are also numerically acquired when processing vibration information in the frequency domain, and methods selected from matrix and vector calculation and methods for system identification in the frequency domain are utilized for acquiring vibration information in the frequency domain.

17. A method according to claim 9, wherein the classification, identification, information compression and output of parameters and the classification, recognition of relationships, information linkage and output of a diagnosis signal is implemented by neural networks in combination with fuzzy logic or by pure fuzzy logic circuits instead of by the first and second neural networks.

* * * * *